US009888895B2

(12) United States Patent
Klingenbeck

(10) Patent No.: US 9,888,895 B2
(45) Date of Patent: Feb. 13, 2018

(54) ANGIOGRAPHIC EXAMINATION METHOD TO IMPLEMENT A ROTATIONAL ANGIOGRAPHY

(71) Applicant: Siemens Aktiengesellschaft, Munich (DE)

(72) Inventor: Klaus Klingenbeck, Aufsess (DE)

(73) Assignee: Siemens Aktiengesellschaft, Munich (DE)

( * ) Notice: Subject to any disclaimer, the term of this patent is extended or adjusted under 35 U.S.C. 154(b) by 715 days.

(21) Appl. No.: 14/549,867

(22) Filed: Nov. 21, 2014

(65) Prior Publication Data
US 2015/0139396 A1 May 21, 2015

(30) Foreign Application Priority Data
Nov. 21, 2013 (DE) .................. 10 2013 223 786

(51) Int. Cl.
*A61B 6/00* (2006.01)
*A61B 6/04* (2006.01)

(52) U.S. Cl.
CPC ............ *A61B 6/504* (2013.01); *A61B 6/4014* (2013.01); *A61B 6/4441* (2013.01); *A61B 6/58* (2013.01); *A61B 6/0457* (2013.01); *A61B 6/4458* (2013.01); *A61B 6/4464* (2013.01)

(58) Field of Classification Search
CPC .............................. A61B 6/0457; A61B 6/504
See application file for complete search history.

(56) References Cited

U.S. PATENT DOCUMENTS

| 7,500,784 | B2 | 3/2009 | Grebner et al. |
| 7,689,042 | B2* | 3/2010 | Brunner ................. A61B 6/466 378/4 |
| 2011/0182492 | A1 | 7/2011 | Grass et al. |
| 2012/0213338 | A1 | 8/2012 | Hartwich et al. |

FOREIGN PATENT DOCUMENTS

| CN | 101283929 A | 10/2008 |
| DE | 10 2007 005 377 A1 | 7/2008 |

OTHER PUBLICATIONS

Patrick Kurp, "AXIOM Artis FD Systems / DynaCT—A Breakthrough in Interventional 3D Imaging," Reprint from Medical Solutions, (2005) p. 46-51.
AXIOM Artis—Quick Guide for Special Examinations—Software Version VB30 and Higher, Siemens AG, Medical Solutions (2006) 1-74.

* cited by examiner

*Primary Examiner* — Dani Fox
(74) *Attorney, Agent, or Firm* — Schiff Hardin LLP

(57) ABSTRACT

In an angiographic examination method to implement rotational angiographies, two x-ray projections of the examination subject are acquired from different acquisition angles, the x-ray projections are segmented to generate the outer contours of the examination subject in both x-ray projections, the outer contours of the examination subject are discretized in both x-ray projections, the coordinates of the focal points of the examination subject are calculated from these discrete points in both x-ray projections, the deviations of the coordinates of the focal points of the examination subject are determined, the deviations of the coordinates are evaluated, and the results of the evaluation are emitted as an output.

9 Claims, 4 Drawing Sheets

ANGIOGRAPHIC EXAMINATION METHOD TO IMPLEMENT A ROTATIONAL ANGIOGRAPHY

BACKGROUND OF THE INVENTION

Field of the Invention

The invention concerns: an angiographic examination method to implement a rotational angiography using at least one x-ray radiator and at least one x-ray image detector, which are attached to the ends of at least one C-arm, a patient support table with a table plate to support a patient with the examination subject, a system control unit, an image system, and a monitor.

Description of the Prior Art

In 3-D imaging with C-arm systems (known as rotational angiography), for example as described by Patrick Kurp in "AXIOM Artis FD Systems/DynaCT—A Breakthrough in Interventional 3D Imaging", Reprint from Medical Solutions, January 2005, pages 46-51, it is important that the examination subject (for example an organ or the head) to be imaged is supported centrally in the isocenter of the angiography apparatus. This central positioning is essential in order to be able to image the entire organ without truncation effects, and in order to achieve an optimal image quality.

In modern methods, it is up to the medical technician to manually implement this centering under x-ray radioscopy, for example as is described on pages 33 and the following in "AXIOM Artis—Quick Guide for Special Examinations—Software Version VB30 and higher" by Siemens AG, Medical Solutions, AX, 2006.

For example, an angiography system to implement such rotation angiographies is known from U.S. Pat. No. 7,500,784 B2, which is explained in the following in connection with FIG. 1.

FIG. 1 shows a biplanar x-ray system (shown as an example) with two C-arms 2 and 2', each held by a stand 1 and 1' in the form of a six-axis industrial or articulated arm robot. At the ends the C-arms 2 and 2' are respectively mounted an x-ray source (for example x-ray radiators 3 and 3' with x-ray tubes and collimators) and x-ray image detectors 4 and 4' as an image acquisition unit. The first stand 1 is mounted to the floor 5, while the second stand 1' can be attached to the ceiling 6.

The C-arms 2 and 2' can be arbitrarily adjusted in space by the articulated arm robot (known from U.S. Pat. No. 7,500,784 B2, for example)—which preferably has six rotation axes and therefore six degrees of freedom. For example, they are rotated around their rotation centers situated between the x-ray receivers 3 and 3' and the x-ray image detectors 4 and 4'. The angiographic x-ray system 1 through 4 according to the invention is in particular rotatable around rotation centers and rotation axes in the C-arm plane of the x-ray image detectors 4 and 4', preferably around rotation axes intersecting the respective middle point of the x-ray image detectors 4 and 4'.

The known articulated arm robot has a base frame that, for example, is permanently mounted on the floor 5 or on the ceiling 6. A carousel is attached to this so as to be rotatable around a first rotation axis. A robot rocker is mounted on the carousel so as to be pivotable around a second rotation axis, on which robot rocker a robot arm is attached so as to be rotatable around a third rotation axis. At the end of the robot arm, a robot hand is attached so as to be rotatable around a fourth rotation axis. The robot hand has an attachment element for the C-arm 2 or 2', which is pivotable around a fifth rotation axis and is rotatable around a six rotation axis orthogonal to the fifth rotation axis.

A table plate 7 of a patient bearing table 8 to accommodate a patient to be examined as an examination subject is located in the beam path of the x-ray radiators 3 and 3'. The patient support table 8 is provided with a control panel 9. Connected to the x-ray diagnostic device is a system control unit 10 with an image system 11 that receives and processes the image signals of the x-ray image detectors 4 and 4' (operating elements are not shown, for example). The x-ray images can then be viewed on displays of a monitor screen mounted by a ceiling-mounted, longitudinally movable carrier system 12. Furthermore, a device 14, whose function will be described in further detail below, is provided in the system control unit 7.

The realization of the x-ray diagnostic device (shown in FIG. 1, for example) is not dependent on the six-axis industrial or articular arm robot with the stands 1 and 1'. In the angiography x-ray system typical C-arm apparatuses with normal ceiling-mounted or floor-mounted retention for the C-arms 2 and 2' can also be used.

Instead of the C-arms 2 and 2' that are shown, for example, the angiographic x-ray system can also have separate ceiling-mounted and/or floor-mounted retentions for the x-ray radiators 3 and 3' and the x-ray image detectors 4 and 4', which are rigidly coupled electronically with one another, for example.

The x-ray image detectors 4 and 4' can be rectangular or quadratic flat semiconductor detectors that are preferably created from amorphous silicon (a-Si). However, integrating (and possibly counting) CMOS detectors can also be used.

SUMMARY OF THE INVENTION

An object of the invention is to provide an angiographic examination method of the aforementioned type that simply enables a central support of the examination subject to be imaged in the isocenter apparatus, from just two x-ray projections.

According to the invention, the above object for an angiography examination method is achieved by the following steps:

S1 generate two x-ray projections of the examination subject from different acquisition angles, S2 segment the x-ray projections to generate the outer contours of the examination subject in both x-ray projections, S3 discretize the contour of the examination subject in both x-ray projections with a sufficient density of points, S4 calculate the coordinates of the focal point of the examination subject from these discrete points in both x-ray projections, S5 determine the deviations of the coordinates of the focal point of the examination subject, S6 assess the deviations of the coordinates, and S7 output the results.

This method according to the invention enables (possibly automatically) a central bearing of the examination subject to be imaged in the isocenter, from just two x-ray projections.

It has proven to be advantageous when, according to method step S1, two orthogonal x-ray projections of the examination subject are acquired, typically a.p. and lateral projection.

According to the invention, the output of the results according to method step S7 can take place as a visualization of the results, or also by means of an adjustment of components based on the results.

In the case of strong local variations of the outer contours of the examination subject, before the method step S3 a smoothing of the contours can advantageously be implemented.

In the case of small differences of the deviations of the coordinates relative to the global dimensions of the examination subject, a communication, display and/or rendering of the two appertaining coordinates can take place according to method step S7a.

It has proven to be advantageous if, in the case of large differences of the deviations of the coordinates relative to the global dimensions of the examination subject, an adjustment of the results takes place according to method step S7b by displacements and/or adjustments of: the table plate, for example a movement of the patient bearing table in the longitudinal direction, in the height and laterally; and/or of at least one of the C-arms; such that the focal point lies in the isocenter of the C-arm.

According to the invention, in the event of large differences of the deviations of the coordinates relative to the global dimensions of the examination subject according to method step S7b, a coordinate correction can be required.

According to the invention, in method step S4, the calculation of the coordinates of the focal points of the examination subject is implemented according to the following equations:

$$Y_s^l = \frac{1}{N}\sum_{i=1}^{N} Y_i, Z_s^l = \frac{1}{N}\sum_{i=1}^{N} Z_i, X_s^{ap} = \frac{1}{N}\sum_{i=1}^{N} X_i \text{ and } Z_s^{ap} = \frac{1}{N}\sum_{i=1}^{N} Z_i.$$

DESCRIPTION OF THE PREFERRED EMBODIMENTS

Figure 2:
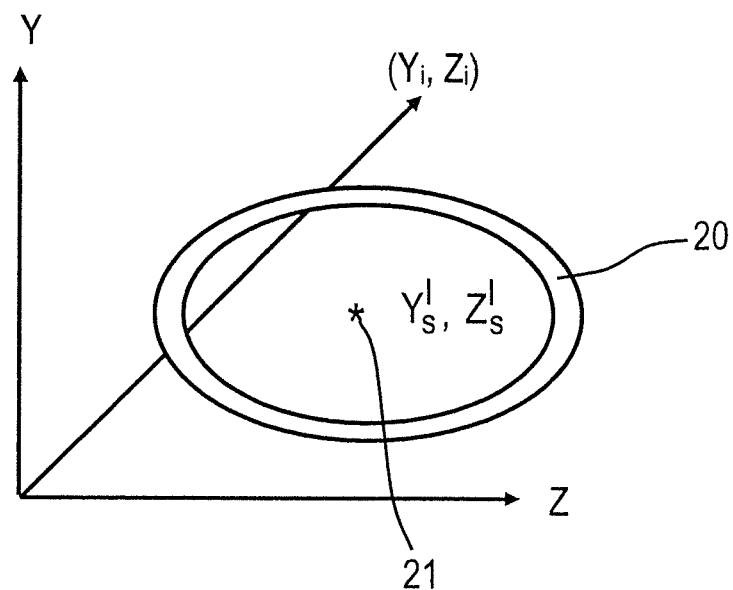
FIG. 2 schematically illustrates a lateral projection image of an examination subject 20 in a coordinate system Y, Z.

A lateral projection image of an examination subject 20—of a skull, for example—is schematically shown as an ellipse in a coordinate system Y, Z in FIG. 2, in a sagittal section.

This contour of the examination subject 20 is discretized with a sufficient density of points ($Y_i$, $Z_i$).

From these discrete points, the lateral focal point 21 ($Y_s^l$, $Z_s^l$) of the examination subject 20 in the lateral projection can be calculated as follows:

$$Y_s^l = \frac{1}{N}\sum_{i=1}^{N} Y_i$$

-continued
and $$Z_s^l = \frac{1}{N}\sum_{i=1}^{N} Z_i.$$

Figure 3:
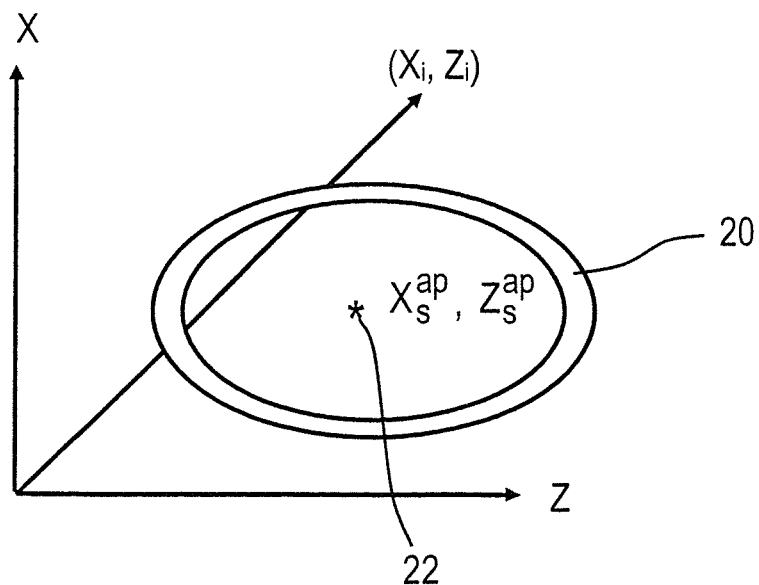
FIG. 3 schematically illustrates an a.p. projection image of an examination subject 20 in a coordinate system X, Z.

FIG. 3 schematically shows a projection image of the examination subject 20 that is preferably aligned orthogonal to the projection image according to FIG. 2, in a coordinate system X, Z, thus a coronary section or, respectively, an a.p. (anterior-posterior) projection image.

From the discrete points of the contour of the examination subject 20, corresponding focal point coordinates of the coronary focal point 22 ($X_s^{ap}$, $Z_s^{ap}$) of the examination subject 20 in the a.p. projection can be calculated as follows:

$$X_s^{ap} = \frac{1}{N}\sum_{i=1}^{N} X_i$$

and $$Z_s^{ap} = \frac{1}{N}\sum_{i=1}^{N} Z_i.$$

Figure 4:
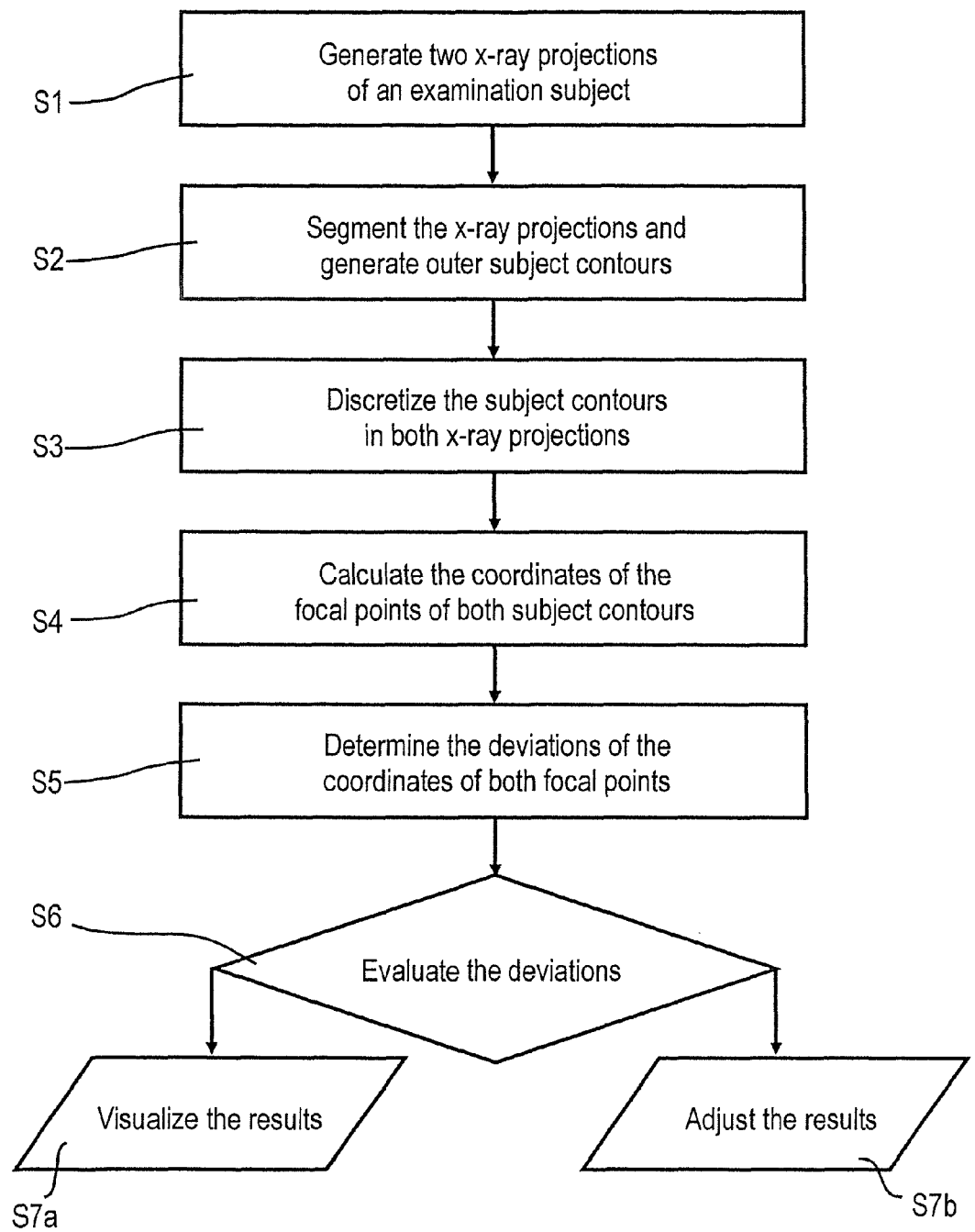
FIG. 4 is a flowchart of an embodiment of the invention for centering the examination subject to be imaged in the isocenter, from two x-ray projections.

Using FIG. 4, the method according to the invention is now explained in detail using the illustration of a head, where the centering of the implementation of rotation angiographies is especially important since a truncation of the skullcap can lead to strong artifacts. For example, this method can be implemented by means of the device 14.

In a first method S1, two x-ray projections of the examination subject 20 are generated at different acquisition angles (for example a.p. and lateral).

As a second method step S2, a segmentation of the x-ray projections is implemented to generate outer subject contours (contours of the examination subject 20) in both x-ray projections—in the present example, of the skull schematically depicted as an ellipse.

In a third method step S3, a discretization of the subject contours of the examination subject 20 in two x-ray projections takes place with a sufficient density of points ($X_i$, $Y_i$ and $Z_i$).

A calculation of the coordinates of the focal points 21 and 22 ($Y_s^l$, $Z_s^l$, $X_s^{ap}$ and $Z_s^{ap}$) of the examination subject 20 from these discrete points in both x-ray projections is implemented in the fourth method step S4.

In a fifth method step S5, the deviations ($Z_s^l$ and $Z_s^{ap}$) of the coordinates of both focal 21 and 22 of the examination subject 20 are determined.

These deviations ($Z_s^l$/$Z_s^{ap}$) are assessed in a sixth method step S6 by comparison with a threshold SW.

This threshold SW depends on the size of the global dimensions of the examination subject 20 and, for example, is selectable by an examination personnel. However, it can also be determined automatically from dimensions of the examination subject 20 that are input by the examination personnel.

According to a seventh method step S7, an output of the result takes place corresponding to the magnitude of the deviation relative to the dimensions of the examination subject 20. If the device is smaller than a predetermined threshold SW depending on the dimensions of the examination subject 20, the output can then take place according to method step S7a via a visualization of the deviations ($Z_s^l/Z_s^{ap}$) or the coordinates of both focal points 21 and 22.

In contrast to this, if the deviation exceeds the predetermined the threshold SW, an adjustment can then be implemented automatically according to method step S7b. For example, this can be achieved via displacements of at least one of the C-arms 2 and/or 2' or of the table plate 7, such that the position of the isocenter in both projections is the same.

Figure 1:
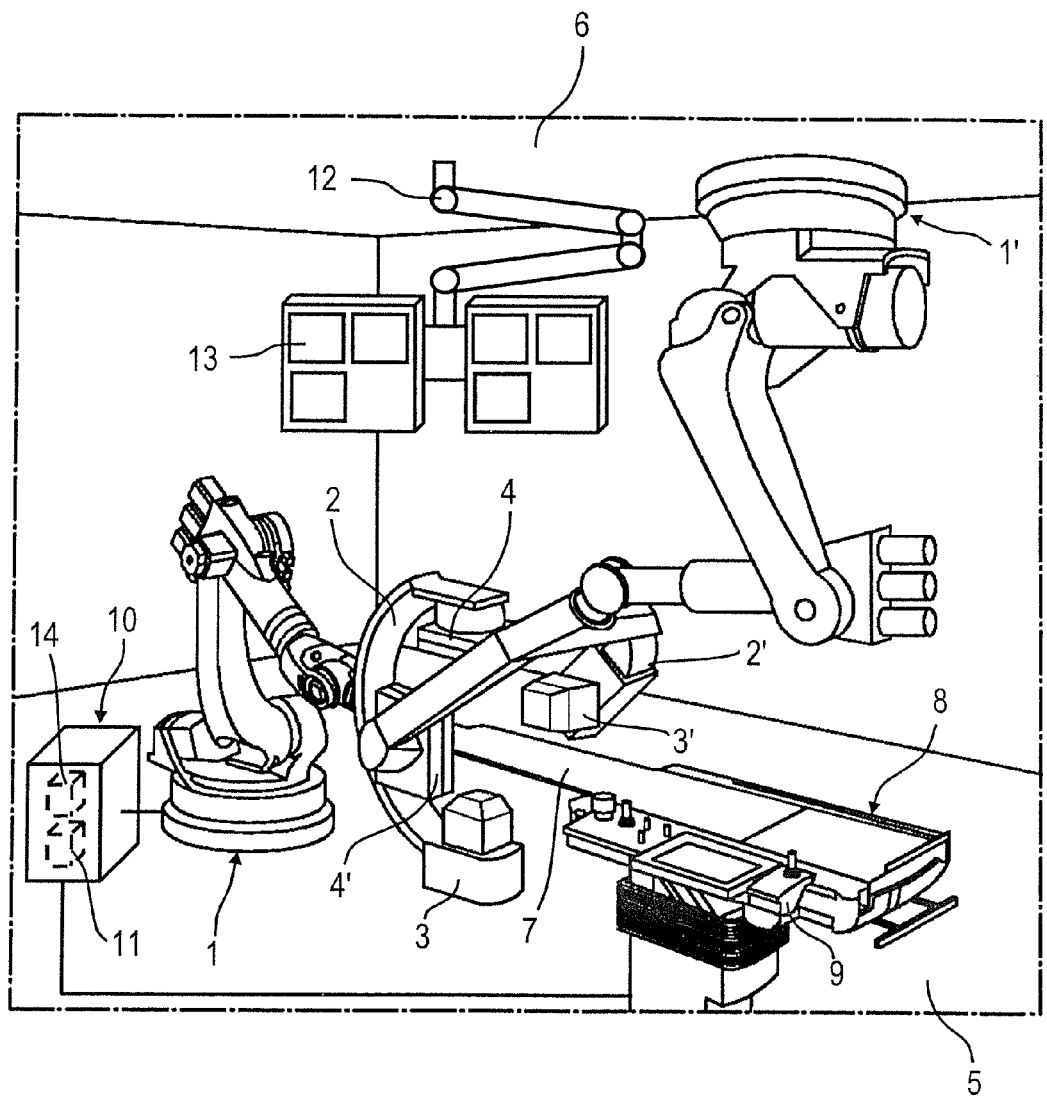
FIG. 1 shows a biplanar C-arm angiography system with respective industrial robots as support devices.
Figure 5:
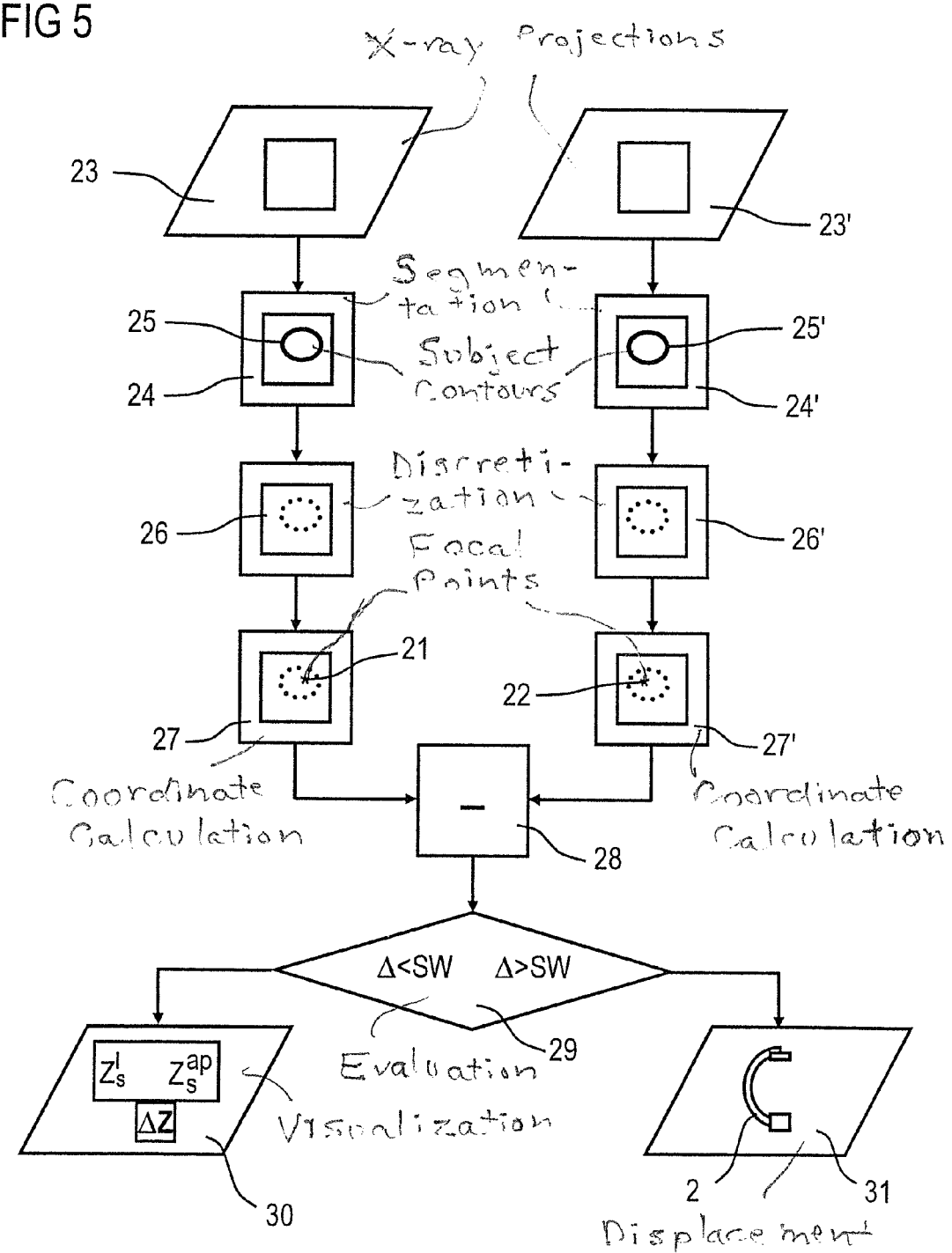
FIG. 5 is another flowchart for explaining the method according to the invention.

FIG. 5 shows a flowchart of the method workflow according to FIG. 4. Initially, two x-ray projections 23 and 23' are acquired. This can take place by means of a biplanar x-ray diagnostic device according to FIG. 1, in which the C-arms 2 and 2' are arranged at an angle that preferably amounts to 90°. However, a monoplanar x-ray system can also be used in which the x-ray projections 23 and 23' with different acquisition angles.

These acquired x-ray projections 23 and 23' are subjected to a segmentation 24 and 24', such that the subject contours 25 and 25' of the examination subject 20 are obtained in both x-ray projections 23 and 23'.

Both subject contours 25 and 25' are subsequent subjected to a discretization 26 and 26' with a sufficient density of points $X_i$, $Y_i$ and $Z_i$.

A coordinate calculation 27 and 27' of the focal points 21 and 22 of both subject contours 25 and 25' takes place by means of these discrete points. A determination 28 of the deviations of the coordinates of both focal points 21 and 22, as well as an evaluation 29 of the deviations, are subsequently implemented.

An output of the result of the evaluation 29 takes place corresponding to the value of the assessed deviations. If the deviation is smaller than a determined threshold SW, the output can then take place by a visualization 30 of—for example—the coordinates $Z_s^l$ and $Z_s^{ap}$ of both focal points 21 and 22, or their deviation AZ.

In contrast to this, if the assessed deviation exceeds the established threshold SW, the position of the isocenter in both projections can be adjusted automatically via displacement 31 of components, at least one of the C-arms 2 and/or 2' and/or the table plate 7.

In summary, this method according to the invention enables central bearing automatically from two orthogonal x-ray projections, typically a.p. and lateral projection.

The lateral projection image of a skull as an examination subject 20 is initially considered, which skull is schematically depicted as an ellipse in FIG. 2.

The skull is first segmented in the projection image. In the present case, the outer subject contour of the skullcap is obtained from this.

This subject contour of the skull is then discretized with a sufficient density of points ($Y_i$, $Z_i$).

In the event that this subject contour has local variations that are too strong, a corresponding smoothing of the subject contour can still also be conducted beforehand.

From these discrete points, the focal point 21 of the subject in the lateral projection can be calculated:

$$Y_s^l = \frac{1}{N}\sum_{i=1}^{N} Y_i$$

and $$Z_s^l = \frac{1}{N}\sum_{i=1}^{N} Z_i.$$

In the case of a circle or an ellipse 20, the focal point 21 is identical to the middle point.

The same procedure is now applied to the a.p. projection image, and corresponding coordinates of the coronary focal point 22 are obtained:

$$X_s^{ap} = \frac{1}{N}\sum_{i=1}^{N} X_i$$

and $$Z_s^{ap} = \frac{1}{N}\sum_{i=1}^{N} Z_i.$$

In the idealized case of an ellipsoid, the coordinates $Z_s^l$ and $Z_s^{ap}$ of the focal points 21 and 22 from both projections coincide. In the real case, differences normally result in the z-coordinates of the focal points 21 and 22 that are determined in such a manner. In the event that these differences are small relative to the global dimensions of the subject, a communication of the two appertaining coordinates can in practice be sufficient.

In contrast to this, if the differences are large, the situation can thus be graphically indicated to the user, and a correction can be required.

In all cases, the table plate 7 of the patient bearing table 8 can be moved in the longitudinal direction, in its height and laterally so that the focal point 21 comes to lie in the isocenter of the respective C-arm 2 or 2'. This method of the patient bearing table 8 can automatically take place via the system, wherein the collision monitoring of the respective C-arm 2 or 2' ensures the safety of the patient. Alternatively, the necessary positions of the patient bearing table 8 can be graphically indicated, and it remains left to the user to approach the indicated (and possibly preset) table positions.

In the event that the C-arms 2 and 2' possess the same mechanical flexibility as (for example) given the robot-based angiography system according to U.S. Pat. No. 7,500,784 B2, given a stationary patient bearing table 8 the necessary displacements in x, y and z can also be realized via the C-arms 2 and 2'.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to operate an angiographic examination system to conduct a rotational angiography of an examination subject around an isocenter of the angiographic examination system, said method comprising:
    (S1) placing an examination subject on a patient support and acquiring two x-ray projections of the examination subject, respectively from different acquisition angles, by rotating at least one C-arm-mounted x-ray radiator and x-ray image detector around the patient on the patient support;
    (S2) providing said two x-ray projections to a computer and, in said computer, automatically segmenting the x-ray projections to generate outer contours of the patient in each of said two x-ray projections;
    (S3) in said computer, automatically discretizing said outer contours in each of said two x-ray projections;
    (S4) in said computer, automatically calculating coordinates of focal points of the patient from discrete points in each of said two x-ray projections produced by said discretization of said outer contours;

(S5) in said computer, automatically determining deviations of said coordinates of the respective focal points of the patient;

(S6) in said computer, automatically evaluating said deviations of said coordinates to produce an evaluation result; and (S7) presenting said evaluation result in a humanly perceptible form as an output from said computer in communication with said computer.

2. A method as claimed in claim 1 comprising, in (S1), acquiring said two x-ray projections as orthogonal x-ray projections of the patient.

3. A method as claimed in claim 1 comprising, in (S7), presenting said examination result visually at a monitor in communication with said computer.

4. A method as claimed in claim 1 comprising adjusting at least said C-arm mounted x-ray radiator and x-ray image detector dependent on said evaluation result to maintain rotation around said patient with respect to said isocenter.

5. A method as claimed in claim 1 comprising, before (S3), smoothing each of said outer contours to smooth local variations in the respective outer contours.

6. A method as claimed in claim 1 comprising, in said computer, identifying dimensions of said patient and comparing said deviations to said dimensions of said patient to obtain a comparison result, and when said comparison result is below a predetermined threshold, presenting said coordinates in a humanly perceptible form as an output from said computer.

7. A method as claimed in claim 6 comprising, when said comparison result exceeds a predetermined threshold, automatically adjusting at least said C-arm to maintain rotation of said C-arm around said isocenter.

8. A method as claimed in claim 7 comprising, at a monitor screen in communication with said computer, graphically indicating a coordinate correction that is needed in order to maintain rotation of said C-arm around said isocenter.

9. A method as claimed in claim 1 comprising, in S4, calculating said coordinates of said focal points according to:

$$Y_s^l = \frac{1}{N}\sum_{i=1}^{N} Y_i,$$

$$Z_s^l = \frac{1}{N}\sum_{i=1}^{N} Z_i,$$

$$X_s^{ap} = \frac{1}{N}\sum_{i=1}^{N} X_i \text{ and}$$

$$Z_s^{ap} = \frac{1}{N}\sum_{i=1}^{N} Z_i.$$

* * * * *